United States Patent [19]

Wagner et al.

[11] Patent Number: 4,978,625

[45] Date of Patent: Dec. 18, 1990

[54] FLUORESCENCE IMMUNOASSAY USING WATER INSOLUBLE DYES

[75] Inventors: Daniel B. Wagner, Raleigh; Glenn P. Vonk, Fuquay-Varina; Thomas J. Mercolino, Chapel Hill, all of N.C.

[73] Assignee: Becton, Dickinson and Company, Franklin Lakes, N.J.

[21] Appl. No.: 109,689

[22] Filed: Oct. 19, 1987

[51] Int. Cl.$^5$ .......................................... G01N 33/543
[52] U.S. Cl. .................... 436/518; 436/528; 436/546; 436/800; 436/808; 436/829
[58] Field of Search .................. 435/7, 810; 436/518, 436/546, 800, 808, 829; 424/38; 514/75–78

[56] References Cited

U.S. PATENT DOCUMENTS

| | | | |
|---|---|---|---|
| 4,058,732 | 11/1977 | Wieder | 250/461 |
| 4,235,792 | 11/1980 | Hsia et al. | 260/403 |
| 4,235,871 | 11/1980 | Papahadjopoulos et al. | 424/19 |
| 4,283,382 | 8/1981 | Frank et al. | 424/8 |
| 4,342,826 | 8/1982 | Cole | 435/7 |
| 4,372,745 | 2/1983 | Mandle et al. | 436/537 |
| 4,373,932 | 2/1983 | Gribnau et al. | |
| 4,374,120 | 2/1983 | Soimi et al. | 436/546 |
| 4,605,630 | 8/1986 | Kung et al. | 436/829 X |
| 4,656,129 | 4/1987 | Wagner | 436/829 X |
| 4,695,554 | 9/1987 | O'Connell et al. | 436/800 X |
| 4,703,017 | 10/1987 | Campbell et al. | 436/518 X |
| 4,717,655 | 1/1988 | Fulioyler | 436/800 X |

FOREIGN PATENT DOCUMENTS 0064484  11/1982  European Pat. Off. .
8500664  2/1985  World Int. Prop. O. .

OTHER PUBLICATIONS

Truneh, A., et al., Journ. Immunol. Methods 100:59–71 (1987).
Raue, R. et al., Heterocycles 21 No. 1: 167–190 (1984).
Dakubu, S. et al., Clin Biochem Anal., 14:71–101 (1984).
Hemmila, I. et al, Anal. Biochem., 137:335–343 (1984).

*Primary Examiner*—Esther L. Kepplinger
*Assistant Examiner*—David A. Saunders
*Attorney, Agent, or Firm*—Richard E. Brown

[57] ABSTRACT

In a method for fluorescence immunoassay of an analyte, an antianalyte attached to the surface of a solid support is contacted with the analyte and a tracer which includes a substantially water insoluble fluorescent dye occluded in the nonaqueous portion of a sac. After binding reactions involving the antianalyte, analyte and tracer, the solid support is separated, excitation light is applied and fluorescence from dye in intact sacs bound to the solid support is measured and compared to fluorescence measured when known quantities of analyte are assayed. The invention includes a kit of materials useful in performing an immunoassay in accordance with the method of the invention.

18 Claims, 1 Drawing Sheet

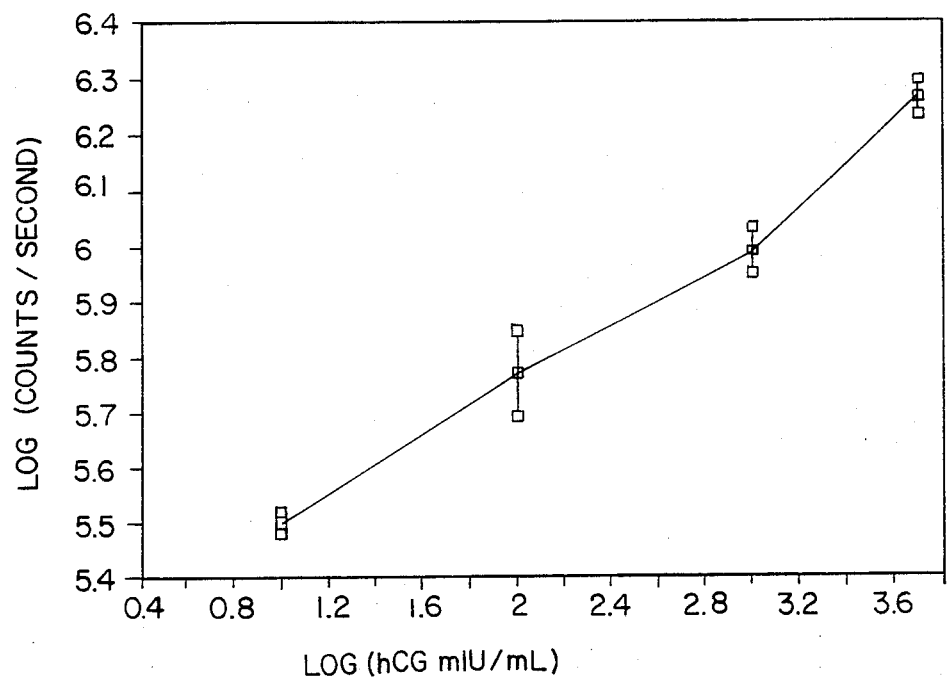

FLUORESCENCE IMMUNOASSAY USING WATER INSOLUBLE DYES

FIELD OF THE INVENTION

This invention relates to an immunoassay of an analyte and materials used therein, and more particularly relates to a method and materials for time resolved immunoassay in which a label is encapsulated in a vesicle.

BACKGROUND OF THE INVENTION

A variety of assay systems which are both rapid and sensitive has been developed to determine the concentration of a substance in a fluid. Immunoassays depend on the binding of an antigen or hapten to a specific antibody and have been particularly useful because they give high levels of specificity and sensitivity. These assays generally employ one of the above reagents in labeled form, the labeled reagent often being referred to as the tracer, and may be carried out in solution or on a solid support.

Radioimmunoassay (RIA) procedures use radioisotopes as labels, provide high levels of sensitivity and reproducibility, and are amenable to automation for rapid processing of large number of samples. However, isotopes are costly, have relatively short shelf lives, require expensive and complex equipment, and extensive safety measures for their handling and disposal must be followed.

Enzymes have also been used as labels in immunoassay. Enzyme immunoassay (EIA) wherein an enzyme label is encapsulated in a vesicle later lysed by complement is disclosed in U.S. Pat. No. 4,235,792 to Hsia et al. and U.S. Pat. No. 4,342,826 to Cole. EIA, although improving on RIA because it does not require precautions against radioactivity, nevertheless has disadvantages. EIA depends on the reaction of the enzyme with a substrate to produce a color which is measured, and thus requires the additional step of providing an enzyme substrate. In addition, sufficient time must be allowed for color development, and an expensive spectrophotometer for measuring color change often must be provided.

Fluoroimmunoassay (FIA), in contrast to EIA, provides direct detection of the label. FIA procedures in which the dyes are entrapped or embedded in either the aqueous phase or the lipid phase of a liposome are disclosed in U.S. Pat. No. 4,372,745 to Mandle et al. and International Published Application No. WO 85/00664 to Kunq et al. In Mandle et al., the liposome is disrupted after a binding reaction and the dye is excited by chemiluminescence generated in the assay medium. Kung et al. is an agglutination assay and requires a large liposome for dye-aided visual detection of an agglutinate.

Known FIA methods using organic fluorochromes, such as fluorescein or rhodamine derivatives, have not achieved the high sensitivity of RIA or EIA, largely because of light scattering by impurities suspended in the assay medium and by background fluorescence emission from other fluorescent materials present in the assay medium. Scattering is particularly troublesome with fluorochromes having a short (50 nm or less) Stoke's shift (the difference between the wavelength of the absorption and emission). For example, the Stoke's shift of fluorescein isothiocyanate is only 20–30 nm. Background fluorescence is particularly troublesome when the assay medium is serum. The sensitivity of an assay in serum may be reduced up to one hundred fold compared to an identical assay in buffer.

The development of time-resolved fluoroimmunoassay (TR-FIA) has contributed to overcoming these problems In this procedure, a fluorochrome label with relatively long fluorescence emission decay time is excited with a pulse of light, and fluorescence emission from the label is measured after a preselected delay. Background emission of short decay time (generally less than 10 ns) essentially ceases during the delay and thereby does not interfere with measurement of the specific emission from the label. TR-FIA is most effective when the fluorescent label has a decay time of 100–1000 ns and a long Stoke's shift (100 nm or greater).

A class of labels meeting the requirements of TR-FIA is the lanthanide chelates. Lanthanide ions, such as ions of europium and terbium, though not fluorescent themselves, form highly fluorescent chelates of long Stoke's shift (up to 250 nm) with organic ligands, in particular with $\beta$-diketones. The ligand portion of the chelate absorbs excitation light and transfers the absorbed energy to the chelated metal ion. The metal ion emits the energy as fluorescence of exceptionally long decay time (1 ms). A discussion of the use of lanthanide chelates in TR-FIA is given in Analytical Biochemistry, 137, 335 (1984) and in Clinical Biochemical Analysis 14, 71 (1984).

U.S. Pat. No. 4,058,732 to Wieder discloses a method and apparatus for use of lanthanide chelates and time resolution in analytical fluorescent spectroscopy.

U.S. Pat. No. 4,283,382 to Frank et al. discloses an improvement in TR-FIA in which a lanthanide chelate label is incorporated into a polymeric bead lattice to eliminate water-induced quenching of the fluorescence emission of the label.

U.S. Pat. No. 4,374,120 to Soini et al. discloses increased stability of lanthanide chelates achieved by a 1:1:1 chelate of lanthanide, $\beta$-diketone, and an aminopolycarboxylic acid analogue having a functional group useful for binding the chelate to a protein.

European Pat. Application EP 0,064,484-A2 discloses a TR-FIA procedure in which the substance to be determined is coupled to a lanthanide by an aminocarboxylic acid analogue, and, after incubation, the lanthanide is split from the substance to be determined and chelated to a $\beta$-diketone before detection.

Copending application Ser. No. 049,971, filed May 15, 1987, of common assignee, discloses a rare earth ion chelate encapsulated in a sac, which ion is fluorescent when released from the sac and complexed with an activator. The sac may be conjugated to a ligand and used in a TR-FIA.

Truneh et al. (Journal of Immunological Methods, 100 59 (1987)) describes enhancement of the fluorescent signal in cell labeling experiments by encapsulating water soluble fluorescein and rhodamine dyes in the aqueous compartment of liposomes, and suggests that intercalating hydrophobic dyes in the liposomal membrane may enable such dyes to be used in similar fashion.

Although lanthanide chelate labels are useful in FIA, several problems exist. Covalent attachment of the chelating agent to a protein component of the assay is a time consuming operation requiring complex chemical reactions under carefully controlled conditions. Such covalent bonding of the chelating agent to the protein may additionally reduce the stability of the subsequently formed chelate, resulting in dissociation of the ion. Dissociation is a particular problem when the labeled protein in the aqueous phase of the assay is in very low concentration. It is toward the solution of these problems that this invention is directed.

SUMMARY OF THE INVENTION

One aspect of the present invention comprises a method for fluorescence immunoassay of an analyte in a fluid. An antianalyte affixed to a solid support is contacted with the fluid and a tracer having an attached medium which occludes a fluorescent dye. After the analyte binds to the antianalyte, bound and free fractions are separated, and the dye in an intact medium is excited. Fluorescence is measured and compared with the magnitude of emission measured when one or more know quantities of analyte is assayed under essentially identical conditions.

The preferred dye is a fluorescent chelated lanthanide ion which is substantially water insoluble and which is occluded in the nonaqueous portion of a sac, most preferably in the lipid portion of a liposome. The most preferred dye is a lanthanide ion chelated with a β-diketone, wherein measurement of fluorescence is performed by time resolution.

In a particularly preferred embodiment of the method, substantially all of the analyte binds to both the antianalyte and the tracer in a sandwich assay. In another preferred embodiment of the method, the tracer and the analyte compete for an insufficient number of antianalyte binding sites in a competitive assay.

Another aspect of the invention includes a kit of materials for performing the method of the invention.

In accordance with the method of the invention, fluorescent dyes which are substantially insoluble in water but substantially soluble in solvents of low polarity are occluded in the lipid bilayer of the sacs. No chemical attachment of the dye to the sac is involved. The dyes do not leak out of the lipid phase of the sac and thus, when the sacs are conjugated by standard methods to a ligand, such as an antigen or antibody, they may be used in an immunoassay for an analyte. In contrast to conventional liposome-based assays, the method of the invention does not include rupture of the sac. Instead, measurement of fluorescence is carried out subsequent to excitation of the dye in the intact liposome by electromagnetic radiation of the appropriate wavelength.

Among the many advantages of the method of the invention are elimination of any chemical manipulation of the dye so that dyes, as for example, Rhodamine 800 (Raue et al., Heterocycles 21, 167 (1984)) may be used in spite of their water insolubility and lack of a functional group suitable for conjugation. Further, fluorescent, water-insoluble lanthanide chelates, such as the β-diketone chelates, can be taken up into liposomes and used in an assay directly in contrast to prior art methods in which water soluble lanthanide chelates of low fluorescence are taken up into the aqueous phase of a liposome, followed by liposome lysis and a fluorescence enhancement step. The method of the present invention may also be compared with prior art methods in which europium ions are conjugated directly to an assay ligand by complex chemical synthesis giving tracers having low ratios of europium ion to ligand.

BRIEF DESCRIPTION OF THE DRAWING

The Figure is a plot of concentration versus fluorescence for assay of human chorionic gonadotropin in accordance with the method of the invention.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the aopended claims and their equivalents.

In accordance with the method of the invention, a substance suspected to be present in a fluid may be detected or its concentration determined by means of an immunological reaction. The substance, hereinafter referred to as the analyte, may be an antigen, a hapten such as a drug or hormone, or an antibody, and may be present in any suitable fluid. For example, the fluid may be a buffer, saline, or a body fluid such as serum or urine. In some cases, the analyte may be isolated from a body fluid and subsequently be introduced into a different fluid, such as buffer, for determination. The preferred analyte is an antigen, for example, a bacterial or viral antigen or an antigenic marker on a cell surface.

By the term "immunological reaction," as used herein, is meant a specific binding reaction of an antigen and an antibody, a hapten and an antibody, or, any appropriate analogue of an antigen, an antibody, or a hapten which also binds specifically. Antibodies useful in this invention may be either polyclonal or monoclonal.

The immunological reaction of the method of the invention is carried out either in solution or preferably, on the surface of a solid support. As known in the art, the solid support may be any support which does not interfere with the assay. Exemplary of solid supports which may be used are glass and polymeric materials, such as polyethylene, polystyrene and the like. Such supports may be fabricated into any suitable shape, such as sheets, plates, wells, strips or tubes. In particularly preferred embodiments of the invention, the immunological reaction is carried out on microtiter strips, in the wells of a microtiter plate or on the inside walls and bottom of a tube, preferably a plastic tube with one closed end.

An antianalyte is attached to the surface of the solid support The antianalyte may be an antigen, an antibody, or an antibody complex having from two to about ten antibodies, which reacts specifically with the analyte, or it may be any appropriate analogue thereof which reacts specifically with the analyte. Attachment of the antianalyte to the solid support may be carried out by an conventional procedure, such as, for example, absorption or covalent bonding. These procedures are well-known in the art, and no further details in these respects are deemed necessary for a complete understanding of the invention.

Subsequent to attachment of the antianalyte to the solid support, any remaining binding sites on the support may preferably be filled with an inert protein, such as, for example, bovine serum albumin, (BSA). Attachment to the inert protein to the solid support is generally carried out by absorption or covalent conjugation.

The quantity of antianalyte to be attached to the solid support depends on the type of assay to be carried out. In a competitive immunoassay, a limited amount of antianalyte is attached, whereby insufficient binding sites are available and the analyte and a tracer for the analyte, described below, compete for the available sites. In a sandwich assay, excess antianalyte is attached whereby essentially all analyte is bound to the antianalyte.

In performing an assay in accordance with the method of the invention, the antianalyte attached to the solid support is contacted with a fluid containing an unknown quantity of analyte, and the assay medium is incubated as described below to induce an immunological reaction between the analyte and antianalyte. A tracer for the analyte is then added, and if necessary, an incubation step may be carried out to induce the immunological reaction. Alternatively and preferably, the analyte and tracer are added simultaneously and a single incubation is carried out. Analyte and tracer bound to the antianalyte on the solid support are hereinafter referred to as the bound fraction, and analyte and tracer which do not bind to the antianalyte are hereinafter referred to as the free fraction.

The tracer provides a means to follow the course of the immunological reaction and preferably consists of a known quantity of the analyte, an antianalyte or appropriate analogue thereof coupled to a label.

The label may be any medium having a dye occluded therein wherein the dye may be fluorescent itself or may be fluorescent when complexed with a suitable agent As known in the art, the occluding medium may be a polymeric microparticle or it may be any one of the wide variety of sacs known in the art. A particularly useful type of sac is a vesicle. Vesicles may be prepared from a wide variety of materials, preferably from lipids. When the vesicle includes a lipid, it is often referred to as a liposome; however, as known in the art, vesicles can be produced from amphiphilic components which are not lipids. As known in the art, liposomes can be prepared from a wide variety of lipids, including phospholipids, glycolipids, steriods, relatively long change alkyl esters, e.g., alkyl phosphates, fatty acid esters, e.g., lecithin, fatty amines and the like. A mixture of fatty materials may be employed such as a combination of neutral steriod, a charged amphiphile and a phospholipid. As illustrative examples of phopholipids there may be mentioned sphingomyelin, dipalmitoyl, lecithin and the like. As representative steriods, there may be mentioned cholesterol, cholestanol, lanosterol and the like. As representative examples of charged amphiphilic compounds, which generally contain from 12 to 30 carbon atoms, there may be mentioned mono or dialkyl phosphate ester, quaternary ammonium salts or an alkylamine; e.g., dicetyl phosphate, distearyl amine, dihexadecyl amine, dilauryl phosphate, dioctadecyl sulfonate, didodecyl dioctylammonium formate, and the like.

Vesicles may be prepared by any one of a wide variety of procedures. Thus, for example, a liposome may be prepared by a reverse emulsion technique, as described in U.S. Pat. No. 4,235,871, wherein there is provided a water-in-oil emulsion containing the materials for forming the vesicle (generally phospholipids), as well as the dye to be occluded in the vesicle, followed by evaporation of the solvent to produce a gel-like mixture which is converted to a vesicle by either agitation or addition of the gel-like mixture to water.

Polymer microcapsules are produced by procedures known in the art, as for example coascervation or interfacial polymerization except that the solution in which the microcapsules are formed also includes a dye whereby the dye is occluded in the polymer microcapsule. The preparation of such microcapsules is disclosed for example in *Microencapsulation Process and Applications,* edited by Jan E. Vandegger (Plenum Press 1974).

In accordance with the invention, the sac or particle may be of any shape, but preferably is substantially spherical. The preferred sacs may be from about 0.01 to 1 um in diameter, most preferably from about 0.05 0.15 um. Liposomes within the desired size range may conveniently be obtained by passage of liposomes of mixed sizes through polycarbonate membrane filters of appropriate pore size.

It is evident that, if the emulsion described above contains both a water soluble dye and water insoluble dye, that the sac prepared therefrom will contain the water insoluble dye occluded substantially in the lipid layer and the water soluble dye encapsulated substantially in the aqueous compartments. The present invention is contemplated to include a tracer having one or more dyes in both the lipid layer and aqueous compartment wherein the fluorescence of the dyes may be read simultaneously. Exemplary of water soluble dyes which are suitable for encapsulation in aqueous compartments of a sac in accordance with this embodiment of the invention are water-soluble fluorescent substances in which the fluorescence is not significantly quenched at the concentration range of 10–100 mM. Examples are: terbium-dipicolinate, calcein blue, and 1,3,6,8-pyrentetrasulfonic acid tetrasodium salt.

Preferred dyes are substantially insoluble in water and soluble in organic solvents whereby they are occluded in the lipid portion of the sac during formation of the sac. Exemplary of such dyes are the carbocyanines, perylenes, and styryls such as 4-dicycano-methylene-2-methyl-6-(p-dimethylaminostyryl)4H-pyran. Particularly preferred dyes are fluorescent chelates of lanthanide ions, for example ions of terbium, samarium, and, most preferably, europium.

Lanthanide ions are only weakly fluorescent until chelated with an appropriate organic molecule. Any organic molecule may be used which provides a fluorescent chelate which is substantially insoluble in water and which is substantially occluded in the lipid layer of the sac. Thus, suitable chelating agents are, for example, substituted phenols, phenanthrolines, and pyridines. Preferred chelating agents are $\beta$-diketones. Exemplary of $\beta$-diketones which can be used are benzoylacetone, dibenzoylmethane, thenoyltrifluoroacetone, benzoyltrifluoroacetone, naphthoyltrifluoroacetone, acetylacetone, trifluoroacetylacetone, hexafluoroacetylacetone, and the like. Chelation of the $\beta$-diketone with the lanthanide ion is routinely carried out by incubating the reagents for an appropriate time. The quantity of lanthanide chelate to be used in preparation of tracer depends on the type of assay to be carried out and the quantity of analyte in the fluid, and is well known to those of ordinary skill in the art.

As indicated above, the sac having the dye therein is referred to as the label, and when coupled to a ligand such as the analyte, antianalyte or appropriate analogue thereof constitutes the tracer. The ligand portion of the tracer may be chosen in accordance with the type of assay to be carried out. In a competitive assay, the ligand to be conjugated to the label is preferably the analyte. In a sandwich assay, the ligand portion of the tracer may be any ligand specific for the analyte, and as such may be a second antianalyte or any appropriate analogue thereof.

The sacs may be coupled to the ligand by a variety of conventional procedures, including covalent coupling, derivatization, activation and the like. In one suitable procedure, the sacs may be coupled to the ligand by the use of an appropriate coupling or spacer compound (one that does not destroy the immunoreactivity of the ligand). As known in the art, the coupling compound has two reactive functional groups, one of which functional groups is capable of reacting or being linked to a functional group of the ligand portion of the tracer, and the other of which is capable of reacting or being linked to a functional group on the sac. For example, the spacer or coupling compound, which includes at least two reactive substituent groups, may contain carboxyl, isocyanate, isothiocyanate, amino, thiol, hydroxy, sulfonyl, carbonyl, etc., substituent groups. The choice of spacer and substituent groups thereon, as should be apparent, is dependent upon the functional groups present in the ligand and sac which are to be coupled to each other.

Alternatively, the sacs may be coupled directly to the ligand. Thus, for example, if the ligand portion of the tracer has an amino substituent group, and the sac portion of the tracer has a carbonyl or carboxyl substituent group, then the ligand and sacs may be directly conjugated to each other by procedures known in the art; for example, an active ester technique.

In still another technique the sacs may be coupled to one of the materials to be used in forming the sacs or by coupling the ligand to the sacs after they are formed. Such procedures are generally known in the art, and no further details in this respect are deemed necessary for a complete understanding of the invention.

As indicated above, the assay medium containing the supported antianalyte, the fluid containing the analyte, and the tracer may be incubated at any temperature and for any length of time suitable to facilitate the immunological reaction and thereby provide the aforementioned bound and free fractions. The incubation may be carried out at a temperature from about 0° to 50° C., preferably from about 30° to 40° C., and may, but need not, result in equilibrium between these fractions.

After completion of any incubation step deemed appropriate, the bound and free fractions may be separated by any appropriate technique such as filtration, decantation or aspiration, the solid phase washed, and the bound label excited with electromagnetic radiation. If desired, the solid phase may be immersed in a liquid such as saline or buffer prior to excitation.

The quantity of analyte present in the fluid may be determined by exciting the bound label with electromagnetic radiation of suitable wavelength and measuring fluorescence emission. When the dye is a lanthanide chelate, excitation radiation is preferably applied as a pulse and emission is preferably measured by time resolution.

Measurement of light emission by time resolution in accordance with the preferred method of the invention is well known in the art and may be carried out in a conventional spectrophotometer, as, for example, a Spex L-111 fluorometer (SPEX Industries, Inc., Edison, N.J.) equipped with a gated photon detector or the "Arcus" time-resolved fluorometer (LKB Diagnostics, Inc. Gaithersburg, Md.).

In a competitive assay, the magnitude of the fluorescence is directly proportional to the quantity of bound tracer and therefore is inversely proportional to the quantity of analyte present in the fluid. In a sandwich assay, the concentration of the analyte present in the fluid is directly proportional to the magnitude of light emission. The concentration of the analyte in the fluid may be determined by comparing the magnitude of fluorescence measured upon assay of the analyte with the fluorescence measured upon assay of a range of known quantities of the analyte assayed under essentially identical conditions.

Another aspect of the invention is a method to label cells using the liposome of the invention having a water insoluble dye occluded substantially in the lipid layer. For example, a liposome having a surface marker, such as phosphatidylcholine (PC), when contacted with a cell expressing a surface antibody recognizing PC, will bind to the antibody, thereby in effect labeling the cell with the water insoluble dye. In another embodiment of this aspect of the invention, the liposome having surface PC may bind to one epitope of an antibody, and a second epitope of the antibody may bind to a cell expressing a surface antigen specific for the second epitope. In still another technique for cell labeling, a cell expressing an antiligand specific for the ligand portion of the tracer may be labeled by binding to the tracer. Thus, a variety of procedures for cell labeling is evident to one skilled in the art, and the invention is intended to include any procedure for cell labeling using the dye-loaded liposome of the invention.

In accordance with another aspect of the invention, there is provided a reagent kit or package of materials for accomplishing an assay for an analyte in accordance with the method of the invention. The kit may include a solid support having attached thereto an antianalyte specific to the analyte, and a tracer for the analyte which includes a sac having therein a dye capable of absorbing excitation radiation and emitting fluorescence. The kit may also include standards for the analyte, as, for example, one or more analyte samples of known concentration, or a fluid sample free of analyte. It may also include other reagents, such as buffers, saline or other labeled or unlabeled specific antigens, antibodies or complexes thereof useful in carrying out the assay. The components of the kit may be supplied in separate containers, as, for example, vials, or two or more of the components may be combined in a single container.

The following examples are provided to further describe the invention, but are in no way to be considered as limitative of the invention.

EXAMPLE I

Assay for Human Chorionic Gonadotropin (hCG) Using Fluorescent Europium Liposomes 1. Preparation of Liposomes Having Fluorescent Europium Chelate Entrapped in the Bilayer of the Liposome Phosphatidylcholine (94 mg , phosphatidylglycerol (10.3 mg), cholesterol (50.9 mg) and phosphati-dylethanolamine-maleiamide reagent (3.75 mg) were dissolved in chloroform. To this solution was added tris-($\beta$-naphthoyltrifluoromethylacetyl-acetonato)-bis-piperazine europium (III) complex (6 mg) and tri(n-octyl)- phosphine oxide (6 mg). The resulting solution was concentrated to a thin film in vacuo overnight. Swell buffer (TRIS 50 mM sodium acetate 50 mM, sodium chloride 50 mM, $10^{-7}$ M europium nitrate, pH 7.0) was added and the flask warmed at 50° to 60° C. to suspend the lipids. The mixture was sonicated with a titanium probe (75 watts, 5×2 min) cooling with ice water between each sonication. The mixture was then centrifuged at low speed to remove titanium particles and extruded through polycarbonate membranes (5, 0.4, and 0.2 u). This mixture was then passed over a sephadex column (G-25, med, 2×30 cm) previously equilibrated and eluted with coupling buffer (TRIS 50 mM, sodium acetate 50 mM, sodium chloride 50 mM, $10^{-7}$ M europium nitrate, pH 8.0). The fluorescent fractions were collected (5 ml/ea), and the two most fluorescent fractions combined. The liposome suspension was then combined with a first monoclonal anti-hCG antibody (2 mg) previously reduced with dithiothreitol (DTT) and purified on sephadex G-25 med. using coupling buffer as eluent. This mixture was allowed to stand overnight in the dark at ambient temperature, then purified by centrifugation (75,000 Xg, 0.5 h) twice in storage buffer (TRIS 50 mM, sodium acetate 50 mM, glycerol 2%, DMSO 0.5 mL/L sodium azide 0.2 g/L, $10^{-7}$ M europium nitrate, pH 7.4, milliosmolality 310). The liposomes were stable for at least one month at 4° C.

2. Microtiter Strips

A solution of a second monoclonal anti-hCG antibody (1.76 ug/mL) in coating buffer (sodium carbonate 1.59 g/L, sodium bicarbonate 2.93 g/L, thimerosal 0.1 g/L pH 9.6) was aliquoted into microtiter strips (200 uL/well, Titretek), covered, and allowed to stand at 4° C overnight. The strips were then washed with phosphate buffered saline (3X). TRIS blocking buffer (TRIS 50 mM, sodium chloride 9 g/L, BSA 0.5%, sodium azide 0.2 g/L, pH 7.7; 300 uL/well) was added and the strips allowed to stand at 4° C. overnight. The blocked strips were washed with HEPES assay buffer (HEPES 50 mM, sodium chloride 9 g/L, BSA, 0.5%, sodium azide 0.2 g/L, pH 7.7; 200 uL/well), and stored humidified at 4° C.

3. Assay Procedure

Serum standards of hCG (LKB, Gaithersburg, MD) were aliquoted into microtiter strips (20 uL/well) and diluted with HEPES assay buffer (200 uL/well). The strips were shaken for 1.5 h, and washed with HEPES assay buffer (6X). A solution of liposomes (250 uL) in HEPES assay buffer (10 mL) was added (200 uL/well) and the strips shaken 1.25 h. The strips were washed with HEPES assay buffer (6X) and read in an Arcus (LKB) fluorometer. A standard curve plotting concentration versus fluorescence was constructed in which the linear range extended from 10 to 5000 mIU hCG per mL. The correlation of expected and observed values was 94%. The curve is shown in the Figure.

EXAMPLE II

Cell Labeling With Fluorescent Europium Liposomes

A suspension of hybridoma cells which express cell surface antibody to PC was adjusted to $5 \times 10^{66}$ cells/mL in Hank's balanced salt solution (HBSS). Serial dilutions of this suspension were placed into V-bottom polystyrene microtiter strips A solution of fluorescent europium liposomes (example 1, 1/40 in HBSS, 50 uL/well) was added. In the same fashion, control lymphoma cells which do not express the surface antibody to PC were run. The strips were washed twice by centrifugation with HBSS and then examined under uv light. The visual detection of 300 cells expressing surface antibody to PC was possible. None of the control cells was fluorescent. Further experiments using the same procedure demonstrated the ability to visually detect 1200 cells with specific antibody to PC in the presence of $10^4$ non-specific control cells. The results were easily documented photographically using Polaroid film and a red filter (high pass at 610 nm). The experiment was again repeated with liposomes loaded with carboxyfluorescein. - The strips were excited with uv light and viewed through a filter (500 nm high pass). In this case, it was not possible to determine specific cell binding due to background fluorescence of the polystyrene plate.

EXAMPLE III

Entrapment of A Water-Insoluble Perylene Dye in the Liposome Bilayer and Use as a Reagent for Cell Sorting Phosphatidylcholine (94 mg), phosphatidylglycerol (10.3 mg), cholesterol (50.9 mg) and N,N'-bis(2,5-ditert-butyl-phenyl)-3,4,9,10-perylene-carboximide (1.5 mg, Aldrich, Milwaukee, Wis.) were dissolved in chloroform and dried to a thin film. Storage buffer was added, and the mixture warmed, sonicated and extruded through polycarbonate membranes in a similar fashion to example 1. Cells expressing surface antibody to PC were allowed to stand in contact with the liposomes for about 15 min. at 0° C. These labeled cells were then placed on an Epics cell sorter (Coulter Diagnostics, Hialeah, Fla.) using excitation at 488 and a 595 high pass filter. Cells which had surface antibodies to PC were clearly distinguished from control cells without surface antibodies to PC.

EXAMPLE IV

Preparation of Phosphorescent Liposomes

Liposomes were prepared with N,N'-bis(2,5-ditertbutyl-phenyl)-3,4,9,10-perylene entrapped in the lipid bilayer according to Example III. Phosphorescence was measured on a Spex fluorometer (excitation: 466 nm; emission; 621 nm; delay: 0.01 milliseconds; window: 0.2 milliseconds) using 5 nm slits and 100 flashes per point. At an approximate overall perylene concentration of $10^{-5}$ M, the phosphorescence measured 518,000 counts over a buffer background of 17 counts.

EXAMPLE V

Preparation of Liposomes Having Both a Fluorescent Dye Encapsulated in the Internal Aqueous Compartment and Entrapped in the Lipid Bilayer A solution of PC (94 mg), phosphatidylglycerol (10.3 mg), cholesterol (50.9 mg), phosphatidylethanol-amine-maleiamide reagent (3.75 mg), tri-n-octylphosphine oxide (6 mg), and tris-(b-naphthoyltrifluoromethylacetylacetonato)-bis-piperazine europium III complex (6 mg) in chloroform is dried to a thin film under reduced pressure To this is added an aqueous solution (20 ml) of tetrasodium 4,7-bis-(4-phenylsulfonato)-1,10-phenanthroline-2,9-dicarboxylate (50 mM) and europium nitrate (50 mM) adjusted to pH 7.0 with NaOH. The mixture is warmed at 45° C and gently agitated to suspend the lipids. The suspended lipids are then extruded through polycarbonate membranes and coupled to reduced antibody according to Example I.

Thus, in accordance with the invention, a method for fluorescence immunoassay includes use of a tracer having a fluorescent dye occluded in the nonaqueous portion of a sac. Because the dyes are occluded in the nonaqueous portion of the sac, water insoluble dyes may be used, thereby greatly extending the range of usable dyes. Further, because there is no direct covalent linkage between the dye and the sac, no functional groups are needed in the dye, and, consequently, the dye can be used as is without any chemical modification. As some of the water-insoluble fluorescent dyes are rather resistant to self-quenching, it is possible to prepare labeled, bio-specific molecules with a high signal-to-molecule ratio ("high specific activity"). The method of the invention, unlike most others, makes it possible to select a fluorescent dye based only on its spectral characteristics. This flexibility opens up the way to the use of dyes which have their maximum emission in the near IR in assays of reduced background using inexpensive lasers in cell sorters and use of modern, inexpensive, solid-state light detectors.

What is claimed is:

1. A method for determining an unknown quantity of an analyte in a liquid comprising:
   (a) contacting a solid support having affixed thereto an antianalyte specific for an analyte with a liquid suspected of containing said analyte and with a tracer comprising a sac with aqueous and nonaqueous portions, said sac including a substantially water insoluble fluorescent lanthanide chelate occluded substantially in the nonaqueous portion of said sac whereby said analyte binds to said antianalyte and said tracer binds to one of said analyte and said antianalyte to give a bound fraction on said support;
   (b) separating said support having bound fraction thereon from said liquid, said bound fraction including an intact sac with said lanthanide chelate therein;
   (c) exciting lanthanide chelate in said intact sac by applying electromagnetic radiation thereto;
   (d) detecting fluorescence from said lanthanide chelate; and
   (e) determining the quantity of said analyte in said liquid by comparing the magnitude of said fluorescence with the magnitude of fluorescence established for a known quantity of the analyte.

2. The method in accordance with claim 1 wherein said tracer binds to said antianalyte and further comprises said analyte having said sac conjugated thereto.

3. The method in accordance with claim 1 wherein said tracer binds to said analyte and further comprises a second antianalyte having said sac conjugated thereto.

4. The method in accordance with claim 1 wherein said solid support further comprises an inert protein which fills binding sites of the support unoccupied by antianalyte.

5. The method in accordance with claim 1 wherein said analyte is selected from the group consisting of an antigen, an antibody and a hapten.

6. The method in accordance with claim 1 wherein said antianalyte is selected from the group consisting of an antigen, an antibody and an antibody complex.

7. The method in accordance with claim 1 wherein said lanthanide chelate includes an ion selected from the group consisting of europium, terbium, and samarium, said ion being chelated to a β-diketone.

8. The method in accordance with claim 1 wherein said electromagnetic radiation is applied as a pulse and said detecting is performed by time resolved fluorescence.

9. The method in accordance with claim 1 further comprising a water soluble lanthanide chelate encapsulated substantially in the aqueous compartment of said sac.

10. The method in accordance with claim 10 further comprising exciting said water soluble dye and detecting fluorescence from said water soluble dye.

11. A method for determining an unknown quantity of analyte present in a liquid sample comprising:
   (a) preparing a mixture by contacting an antianalyte attached to the surface of a solid support with a liquid containing an unknown quantity of an analyte and a tracer, said tracer comprising a liposome occluding a substantially water insoluble fluorescent lanthanide chelate substantially in the lipid portion thereof, said liposome being conjugated to one of said analyte and a ligand specific to said analyte;
   (b) incubating said mixture to give a bound fraction on sad support;
   (c) separating said support having bound fraction thereon from said mixture, said bound fraction including an intact liposome with said chelate therein;
   (d) exciting chelate in said intact liposome by applying electromagnetic radiation thereto;
   (e) detecting time resolved fluorescence from said chelate; and
   (f) determining the quantity of said analyte in said sample by comparing the magnitude of said fluorescence with the magnitude of fluorescence detected when a mixture containing a known quantity of said analyte is determined in accordance with steps (a) to (e).

12. The method in accordance with claim 11 wherein said ligand is selected from the group consisting of an antigen, an antibody and bound antigen-antibody complex.

13. A kit of materials for performing an assay for an unknown quantity of an analyte in a liquid comprising (1) a solid support having attached thereto an antianalyte specific to an analyte and (2) a tracer for said analyte, said tracer comprising a substantially water insoluble fluorescent lanthanide chelate occluded in a nonaqueous portion of a sac having aqueous and nonaqueous portions, said tracer being conjugated to one of said analyte and a ligand specific to said analyte.

14. The kit in accordance with claim 13 wherein said ligand is selected from the group consisting of an antigen, antibody and a bound antigen-antibody complex.

15. The kit in accordance with claim 13 further comprising a reagent selected from the group consisting of a buffer and saline.

16. The kit in accordance with claim 13 further comprising at least one liquid containing analyte of known concentration.

17. The kit in accordance with claim 13 further comprising a liquid substantially free of analyte.

18. The kit in accordance with claim 13 further comprising a water soluble lanthanide chelate encapsulated substantially in an aqueous compartment of said medium.

* * * * *